(12) United States Patent
Govro et al.

(10) Patent No.: US 9,710,820 B1
(45) Date of Patent: Jul. 18, 2017

(54) SYSTEMS AND MODULES FOR IMPROVING PATIENT SATISFACTION

(71) Applicant: Sphere3, LLC, Kansas City, MO (US)

(72) Inventors: Kourtney Govro, Peculiar, MO (US); Kristal Rayson, Independence, MO (US); Steven Kent Mills, Overland Park, KS (US); Kyle Evans, Faucett, MO (US); David Govro, Peculiar, MO (US)

(73) Assignee: Sphere3, LLC, Kansas City, KS (US)

( * ) Notice: Subject to any disclaimer, the term of this patent is extended or adjusted under 35 U.S.C. 154(b) by 0 days.

(21) Appl. No.: 14/203,280

(22) Filed: Mar. 10, 2014

Related U.S. Application Data

(63) Continuation of application No. 13/795,501, filed on Mar. 12, 2013.

(Continued)

(51) Int. Cl.
*G06Q 50/22* (2012.01)
*G06Q 30/02* (2012.01)

(52) U.S. Cl.
CPC ......... *G06Q 30/0203* (2013.01); *G06Q 50/22* (2013.01)

(58) Field of Classification Search
CPC ... A61B 5/0002; A61B 5/002; A61B 5/02055; A61B 5/11; A61B 5/1115; A61B 5/7246; A61B 5/4809; G06Q 50/22; G06Q 10/0639; G06Q 30/01; G06Q 30/0203; G06Q 30/0282; G06Q 50/24; G06Q 30/0202; G08B 21/0211; G08B 21/0461;

(Continued)

(56) References Cited

U.S. PATENT DOCUMENTS 6,151,581 A * 11/2000 Kraftson ............... G06F 19/327
705/2
7,769,626 B2  8/2010 Reynolds
(Continued)

OTHER PUBLICATIONS

File History of U.S. Appl. No. 13/795,501, filed Mar. 12, 2013, and entitled Systems and Modules for Improving Patient Satisfaction; Applicant: Sphere3, LLC.

(Continued)

*Primary Examiner* — Anita Coupe
*Assistant Examiner* — Gerald Vizvary
(74) *Attorney, Agent, or Firm* — Erise IP, P.A.

(57) ABSTRACT

Systems, modules, and methods set forth herein may allow patient satisfaction to be improved. One system for improving patient satisfaction includes computer readable media, an output device, a processor in data communication with the computer readable media and the output device, and electronic instructions that, when executed by the processor, perform steps for: (a) automatically storing event data from a plurality of electronic devices in the computer readable media; (b) storing perception data obtained from a plurality of patients in the computer readable media; (c) accessing the event data; (d) accessing the perception data; (e) determining at least one correlation between the event data and the perception data; (f) determining at least one proposal to improve patient satisfaction based on the at least one correlation; and (g) actuating the output device to convey the at least one proposal to improve patient satisfaction.

19 Claims, 5 Drawing Sheets

Related U.S. Application Data

(60) Provisional application No. 61/772,283, filed on Mar. 4, 2013.

(58) Field of Classification Search
CPC ...... G06F 50/22; G06F 19/322; G06F 19/327; G06F 19/363; G06F 19/3443; A61M 2205/505; A61M 2230/62; A61M 2230/63; A61G 7/00
USPC .................. 705/2, 3; 340/573.1; 600/306
See application file for complete search history.

(56) References Cited

U.S. PATENT DOCUMENTS

| | | | |
|---|---|---|---|
| 8,972,272 B1* | 3/2015 | Dvorak et al. ................... | 705/3 |
| 2002/0010596 A1* | 1/2002 | Matory ............................ | 705/2 |
| 2004/0122704 A1 | 6/2004 | Sabol et al. | |
| 2005/0010165 A1 | 1/2005 | Hickle | |
| 2006/0181424 A1* | 8/2006 | Graves et al. ............. | 340/573.1 |
| 2007/0150024 A1 | 6/2007 | Leyde et al. | |
| 2008/0059230 A1 | 3/2008 | Manning et al. | |
| 2008/0133290 A1* | 6/2008 | Siegrist et al. ................... | 705/7 |
| 2009/0198509 A1* | 8/2009 | Dumoff ............................. | 705/2 |
| 2010/0241455 A1* | 9/2010 | Gilbert et al. ................... | 705/3 |
| 2011/0112852 A1* | 5/2011 | Ware et al. ....................... | 705/2 |
| 2011/0153349 A1* | 6/2011 | Anderson et al. ............... | 705/2 |
| 2011/0225006 A1 | 9/2011 | Manning et al. | |
| 2012/0078661 A1 | 3/2012 | Sheldon et al. | |
| 2012/0323090 A1* | 12/2012 | Bechtel ............... | A61B 5/6889 600/306 |
| 2012/0330677 A1* | 12/2012 | Velimesis ........................ | 705/2 |
| 2013/0245389 A1 | 9/2013 | Schultz et al. | |
| 2013/0325508 A1 | 12/2013 | Johnson et al. | |
| 2014/0019468 A1 | 1/2014 | Federoff et al. | |

OTHER PUBLICATIONS

File History of U.S. Appl. No. 14/328,533, filed Jul. 10, 2014, and entitled Systems and Methods for Disrupting Undesirable Outcomes; Applicant: Sphere3, LLC.

* cited by examiner

SYSTEMS AND MODULES FOR IMPROVING PATIENT SATISFACTION

RELATED APPLICATIONS

This application is a continuation of U.S. patent application Ser. No. 13/795,501, filed Mar. 12, 2013, which claims priority to provisional application Ser. No. 61/772,283 filed Mar. 4, 2013, the disclosures of which are incorporated herein in their entireties by reference.

BACKGROUND

To date, advances in medicine and healthcare have not directly translated to improvements in patient satisfaction about the care that they have received. Even when a medical outcome is positive, patients may view the care unfavorably if their experience receiving the care failed to meet their expectations. Systems, modules, and methods set forth herein may allow patient satisfaction to be improved.

SUMMARY

The following presents a simplified summary of the invention in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere.

In one embodiment, a system for improving patient satisfaction includes computer readable media, at least one output device, at least one processor in data communication with the computer readable media and the at least one output device, and electronic instructions that, when executed by the at least one processor, perform steps for: (a) automatically storing event data from a plurality of electronic devices in the computer readable media; (b) storing perception data obtained from a plurality of patients in the computer readable media; (c) accessing the event data; (d) accessing the perception data; (e) determining at least one correlation between the event data and the perception data; (f) determining at least one proposal to improve patient satisfaction based on the at least one correlation; and (g) actuating the at least one output device to convey the at least one proposal to improve patient satisfaction.

In another embodiment, a system for improving patient satisfaction includes computer readable media, at least one output device, at least one processor in data communication with the computer readable media and the at least one output device, and electronic instructions that, when executed by the at least one processor, perform steps for: (a) automatically storing event data from a plurality of electronic devices in the computer readable media, the plurality of electronic devices being at multiple locations, the event data being associated with the locations to maintain a record of origin for the event data; (b) storing perception data obtained from a plurality of patients in the computer readable media, the plurality of patients being at the multiple locations, the perception data being associated with the locations to maintain a record of origin for the perception data; (c) accessing the event data; (d) accessing the perception data; (e) determining at least one correlation at a location level between the event data and the perception data; (f) determining at least one correlation at a multi-location level between the event data and the perception data; (g) determining at least one proposal to improve patient satisfaction based on the at least one correlation at the location level; (h) determining at least one proposal to improve patient satisfaction based on the at least one correlation at the multi-location level; (i) actuating the at least one output device to convey the at least one proposal to improve patient satisfaction based on the at least one correlation at the location level; and (j) actuating the at least one output device to convey the at least one proposal to improve patient satisfaction based on the at least one correlation at the multi-location level.

In still another embodiment, a module is provided for use in a system to improve patient satisfaction. The module includes instructions stored on computer readable media that, when executed by at least one processor, perform steps for: (a) accessing event data stored in computer readable media, the event data being automatically input for storage from a plurality of electronic devices; (b) accessing perception data stored in computer readable media, the perception data being obtained from a plurality of patients; (c) determining correlations between the event data and the perception data; (d) determining at least one proposal to improve patient satisfaction based on the correlations; and (e) actuating at least one output device to convey the at least one proposal to improve patient satisfaction.

DETAILED DESCRIPTION

Figure 1:
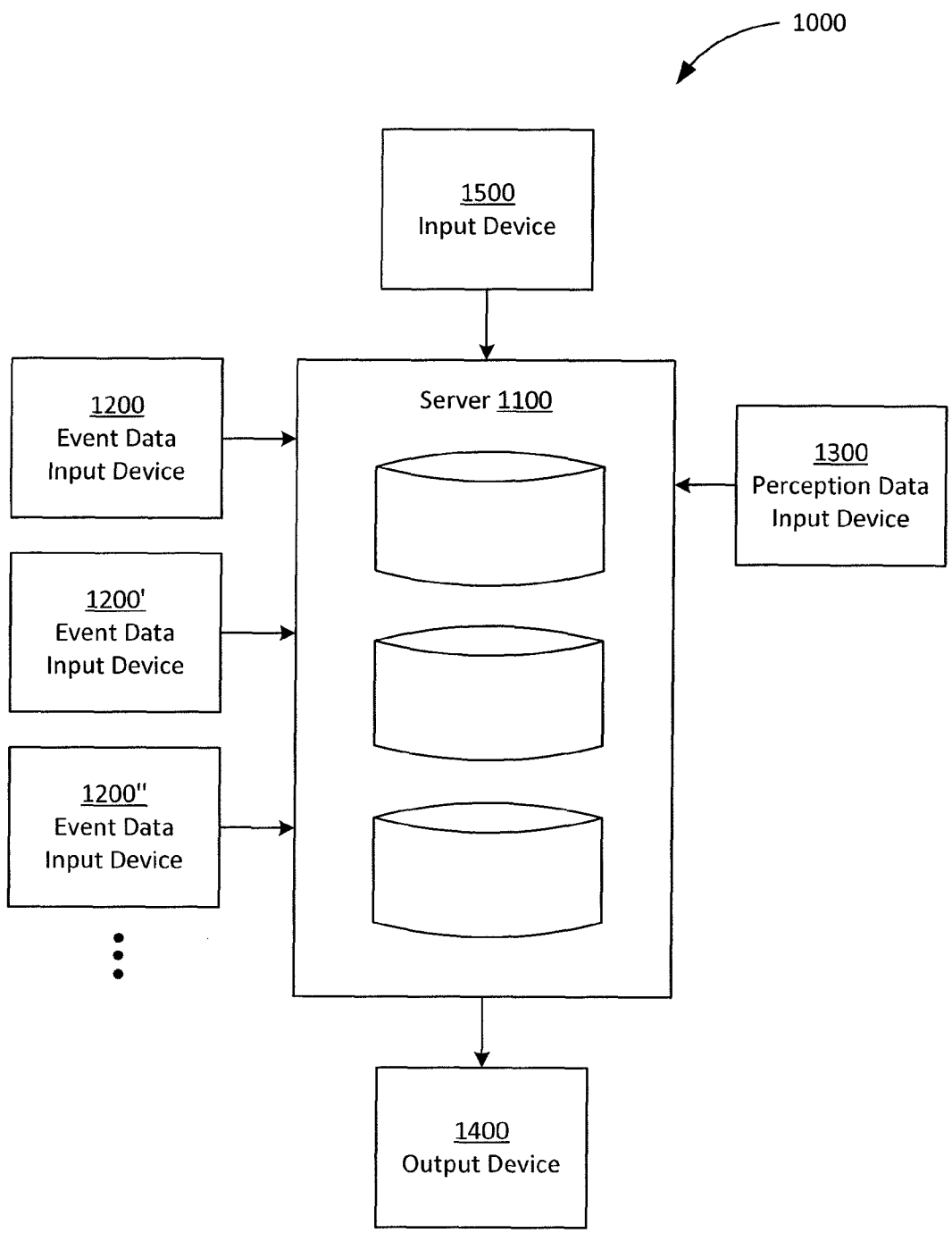
FIG. 1 shows a schematic overview of a system according to one embodiment of the current invention, in use at a single location.

FIG. 1 shows a schematic overview of a system 1000 for improving patient satisfaction according to an embodiment of the current invention, in use at a single location. In broad terms, the system 1000 includes a server 1100, multiple event data input devices 1200 (distinguished in FIG. 1 as 1200, 1200', 1200", etc.), at least one perception data input device 1300, at least one output device 1400, and at least one input device 1500. Those skilled in the art will appreciate that various elements discussed herein may be separated into multiple elements or portions (residing at either the same place, or at different places), or may adversely be combined into fewer elements and portions. For example, the server 1100 may in use be either one server or multiple servers in communication with one another. Or the output device 1400 and the input device 1500 may either be separate devices (the output device 1400 may be a printer, a monitor, etc., while the input device 1500 may be a keyboard, a computer mouse, a touch pad, etc.) or combined into a single device (e.g., a touchscreen). Such integration and separation is insignificant unless otherwise set forth herein or as would be apparent to one of ordinary skill in the art.

Figure 2:
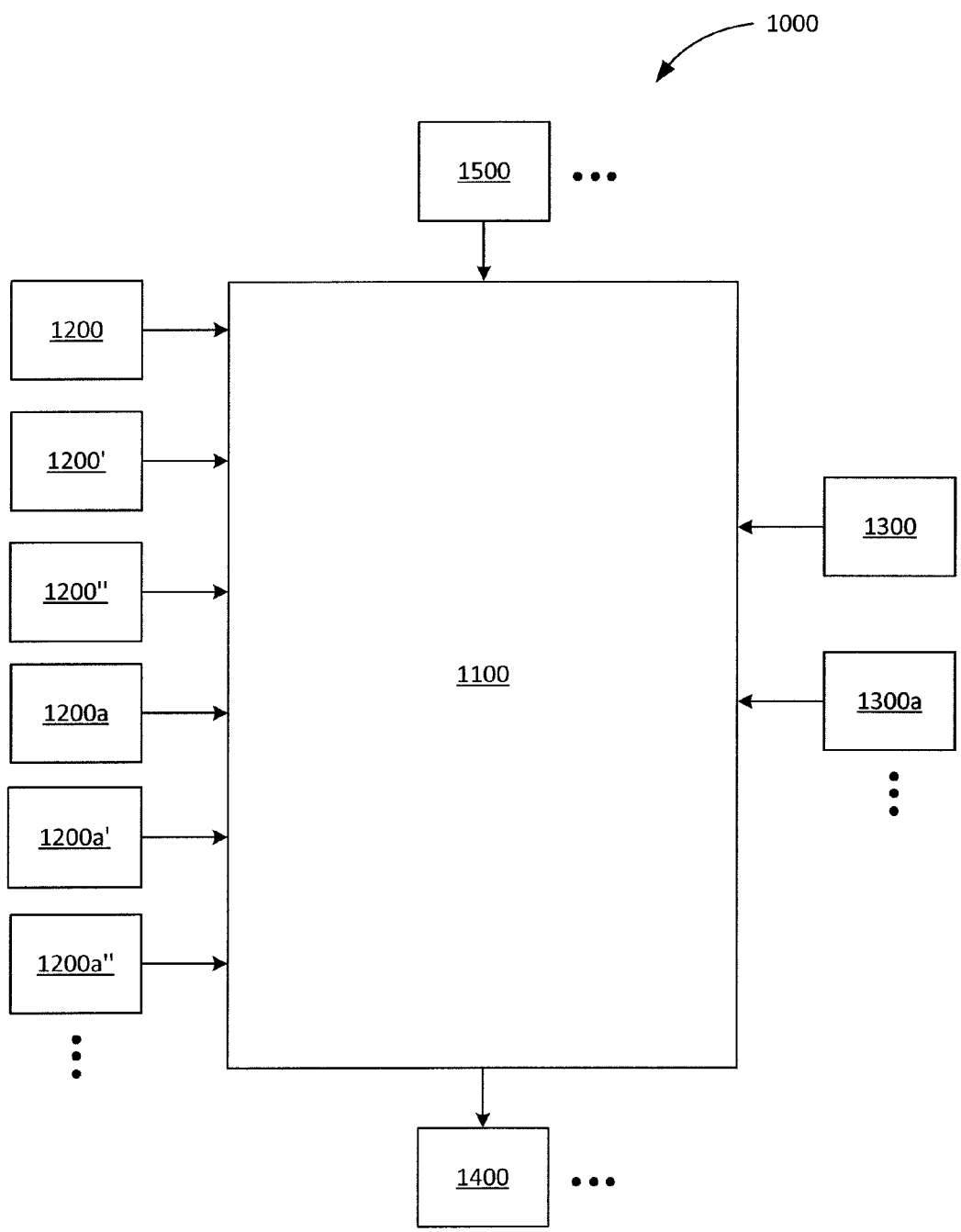
FIG. 2 shows a schematic overview of the system of FIG. 1, in use at multiple locations.

FIG. 2 shows the system 1000 in use at multiple locations. Specifically, additional event data input devices 1200 (distinguished in FIG. 2 by the suffix "a": 1200a, 1200a', 1200a") and an additional perception data input device 1300 (also distinguished in FIG. 2 by the suffix "a": 1300a) are shown. The term "location" is used herein broadly, and may be considered (for example) a patient room; a particular hall, floor, or unit within a medical facility; an entire medical facility; medical facilities within a geographic area; or similar medical units (cardiology, oncology, etc.) within a geographic area. In contrast, the term "location level" is used to refer to locations within a single medical facility, while the term "multi-location level" is used to refer to locations that are not housed within a single medical facility (e.g., medical facilities within a geographic area, or similar medical units within a geographic area). A time component or unique patient identifiers may additionally be utilized within the terms "location", "location level", and "multi-location level", such that (for example) data associated with patient room(s) at a particular time—and thus particular patients—may be analyzed.

Figure 3:
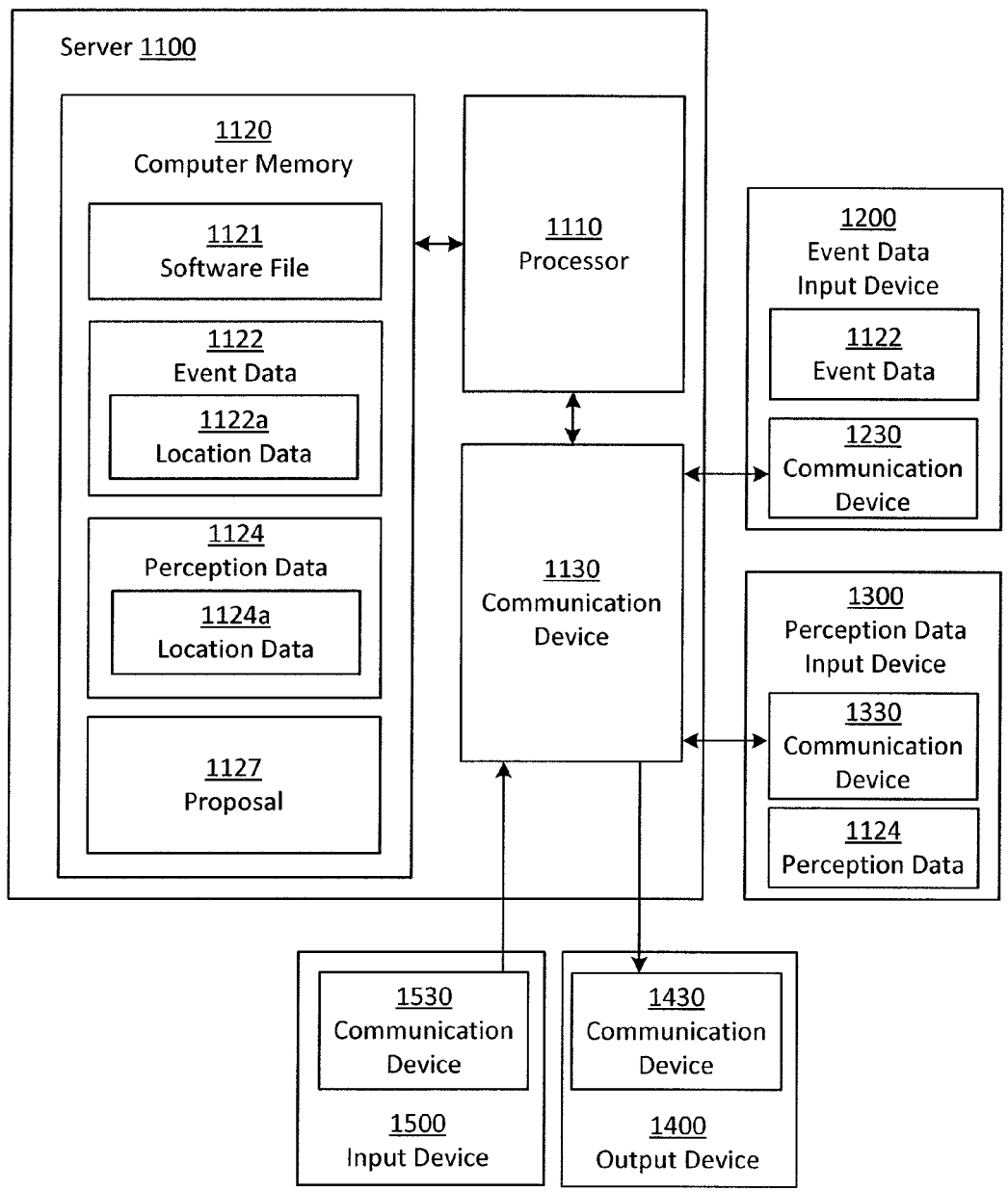
FIG. 3 shows a more detailed view of the system of FIG. 1.

Turning now to FIG. 3, elements of the system 1000 are shown in greater detail. The server 1100 includes a processor 1110 in data communication with computer memory 1120 and a communication device 1130. As discussed above, the processor 1110, the computer memory 1120, and the communication device 1130 may in some embodiments be separated into multiple elements and optionally dispersed.

The computer memory 1120 may include volatile and nonvolatile memory, and any appropriate data storage devices whether now existing or later developed may be used. The computer memory 1120 may store a software file 1121, event data 1122, perception data 1124, and proposal 1127, each of which is discussed further below. In addition, location data 1122a may be associated with the event data 1122 to maintain a record of origin for the event data (i.e., where the event data 1122 came from, and what location should be associated with the event data 1122), and location data 1124a may similarly be associated with the perception data 1124 to maintain a record of origin for the perception data.

The communication device 1130 may be any device, whether now known or later developed, that allows the processor 1110 to communicate with the event data input devices 1200, the perception data input devices 1300, the output devices 1400, and the input devices 1500. For example, the communication device 1130 may be a modem and/or a port for providing wired access to the processor 1110.

Moving on, the event data input devices 1200 may be any device that obtains event data 1122 and interacts automatically with the server 1100 to store the event data 1122 in the computer memory 1120 (either by pushing the event data 1122 to the server 1100, or by the server 1100 pulling the event data 1122 from the event data input devices 1200). Event data 1122 is data relating to a patient, the patient's care, or the patient's location, and may include data regarding: a patient's vital signs, activation of a nurse call light, operation a ventilator device, operation of an IV pump, injuries sustained in the medical facility (e.g., due to falls), the patient's medical condition, temperature of the patient's location (e.g., temperature in a patient's room), staffing levels at the patient's location, the presence of nursing staff, et cetera. Example event data input devices 1200 include interactive beds, telemetry systems, ventilator systems, IV pumps, electronic medical record systems, thermometers, nurse call light systems, and RTLS/RFID locating systems. In some embodiments, the location data 1122a is input to the computer memory 1120 from the event data input devices 1200, while in other embodiments the location data 1122a is added to the computer memory 1120 by the server 1100.

The perception data input devices 1300 may be any device that obtains perception data 1124 and allows the perception data 1124 to be stored in the computer memory 1120. Perception data 1124 is data relating to how patients perceive the care that they have been given. Example perception data input devices 1300 include computer systems through which the patients may respond to surveys about their care and computer systems that digitize non-electronic (e.g., paper or telephone) survey responses. In some embodiments, the location data 1124a is input to the computer memory 1120 from the perception data input devices 1300, while in other embodiments the location data 1124a is added to the computer memory 1120 by the server 1100.

The output device 1400 and the input device 1500 may be any appropriate devices, whether now existing or later developed, for providing data to and presenting data from the processor 1105. As noted above, this may include (for example) a printer, a monitor, a keyboard, a computer mouse, a touch pad, and a touchscreen. The output and input devices 1400, 1500 are shown to respectively have communication devices 1430, 1530 for communicating with the communication device 1130.

Figure 4:
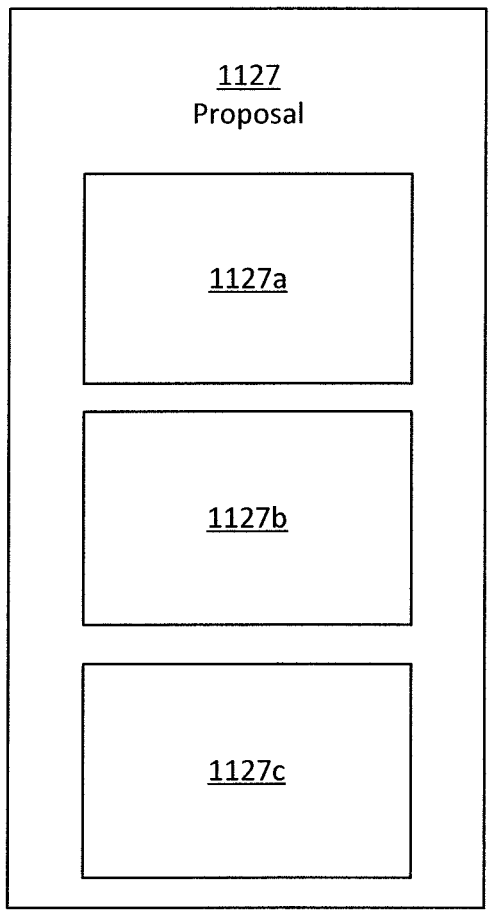
FIG. 4 shows a more detailed view of the proposal of FIG. 3.
Figure 5:
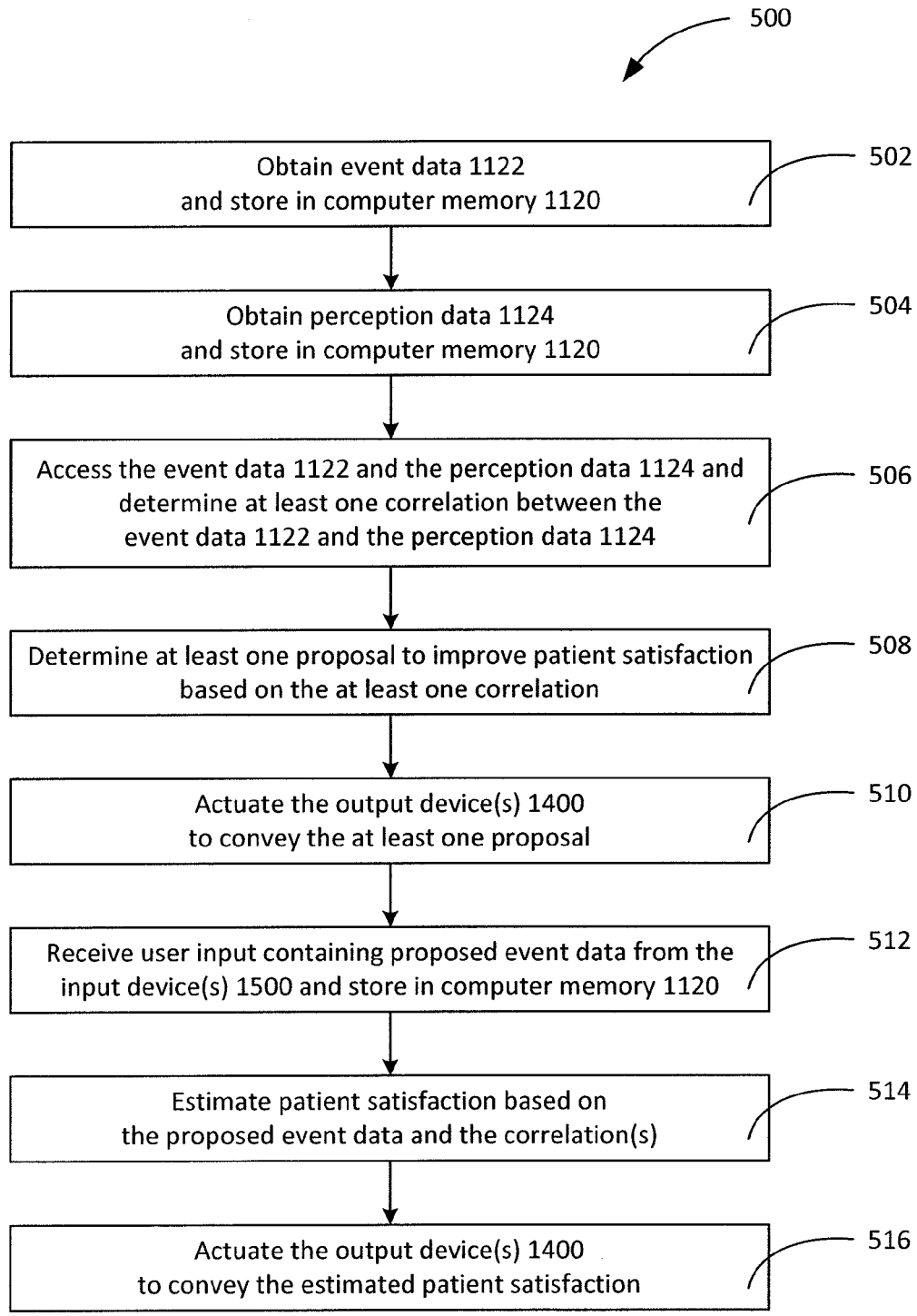
FIG. 5 shows an exemplary set of steps performed by the system of FIG. 1.

Still referring to FIG. 3, the software file 1121 (shown in the server 1100) includes computer instructions for operating the system 1000. In some embodiments, the software file 1121 may be dispersed or duplicated (e.g., in the input devices 1200, 1300). The following description, which references FIGS. 4 and 5, is an example of a process 500 performed by the system 1000 operating in accordance with the software file 1121. Those skilled in the art will appreciate that various described steps may be performed in alternate orders, combined together, or broken into additional steps.

At step 502 (FIG. 5), the event data 1122 is obtained from the event data input devices 1200 and stored in the computer memory 1120. This preferably occurs by the event data input devices 1200 automatically pushing the event data 1122 to the server 1100, or by the server 1100 automatically pulling the event data 1122 from the event data input devices 1200. However, user intervention may be required to provide at least some of the event data 1122 to the server 1100 (e.g., through entering a "send" or "retrieve" command in the devices 1200 or the server 1100). The location data 1122a may be input to the computer memory 1120 from the event data input devices 1200 along with other event data 1122, or the location data 1122a may be added to the computer memory 1120 by the server 1100. The process continues to step 504.

At step 504, the perception data 1124 is obtained from the perception data input devices 1300 and stored in the computer memory 1120. The perception data input devices 1300 may automatically push the perception data 1124 to the server 1100, the server 1100 may automatically pull the perception data 1124 from the perception data input devices 1300, or user intervention (e.g., entering a "send" or "retrieve" command) may cause the perception data 1124 to reach the server 1100. The location data 1124a may be input to the computer memory 1120 from the perception data input devices 1300 along with other perception data 1124, or the location data 1124a may be added to the computer memory 1120 by the server 1100. The process continues to step 506.

At step 506, the processor 1110 accesses the event data 1122 and the perception data 1124 and determines at least one correlation between the event data 1122 and the perception data 1124. From step 506, the process continues to step 508.

At step 508, the processor 1110 determines at least one proposal 1127 to improve patient satisfaction based on the at least one correlation. As illustrated in FIG. 4, multiple proposals 1127 (labeled 1127a, 1127b, 1127c) may be determined. It may be particularly desirable for the proposal(s) 1127 to have an intended effect of improving patient satisfaction in a sufficient amount to meet a predetermined benchmark. In some embodiments, at least one proposal 1127 (e.g., proposal 1127a) is directed to increasing responsiveness (or in other words, increasing services) while at least one other proposal 1127 (e.g., proposal 1127b) is directed to decreasing responsiveness (or in other words, decreasing services). In such embodiments, the proposals 1127 may be determined in a manner intended to have an overall effect of improving patient satisfaction. In some embodiments, the processor 1110 may interact with a pricing or cost module (e.g., a database associating estimated costs with specific actions) to estimate increases/decreases in cost associated with taking various actions, and this data may be considered when determining the proposal(s) 1127 so that a net increase in cost associated with the proposal(s) is minimized or eliminated.

Particularly when the system 1000 is used at multiple facilities, correlations between the event data 1122 and the perception data 1124 may be determined at both a location level and a multi-location level in step 506. At step 508, then, proposal(s) 1127 may be made at both the location level and the multi-location level to improve patient satisfaction.

The process continues from step 508 to step 510, where the processor 1110 actuates the at least one output device 1400 to convey the proposal(s) 1127 to a user. From step 510, the process continues to step 512.

At step 512, the processor 1110 receives user input containing proposed event data from at least one of the input devices 1500 and stores the proposed event data in the computer memory 1120. The process continues to step 514, where the processor 1110 estimates patient satisfaction based on the proposed event data and the at least one correlation from step 506. The processor 1110 then actuates the at least one output device 1400 at step 516, conveying the estimated patient satisfaction to the user. As such, steps 512, 514, and 516 may allow users to see the likely outcomes in patient satisfaction if various actions (represented by the proposed event data) are taken. The proposed event data may vary the proposal(s) 1127 or entirely disregard the proposal(s) 1127.

For illustration, an example use of the process 500 performed by the system 1000 operating in accordance with the software file 1121 will now be provided (again with reference to FIG. 5 and the steps discussed above). This example involves a hospital system having multiple facilities in a city.

At the step 502, the event data 1122 (patient demographics, admit reasons, patients' medical conditions, patients' vital signs, activations of nurse call lights, operation of ventilator devices, operation of IV pumps, injuries sustained in the medical facility, temperatures in patient rooms, staffing levels in the facilities, validated rounding of nurses, physical condition of the facilities, awards received by the facilities, advertising expenditures of the facilities, amenities available in the facilities, et cetera) is obtained from the event data input devices 1200 (electronic medical record systems, interactive beds, telemetry systems, nurse call light systems, RTLS/RFID locating systems, ventilator systems, IV pumps, thermometers, keyboards, et cetera) at the various facilities and stored in the computer memory 1120 with the respective location data 1122a.

At the step 504, the perception data 1124 (perceptions of attentiveness, responsiveness, pain management, facility comfort, facility amenities, facility condition, facility prestige, et cetera) from the patients at the various facilities is obtained from the perception data input devices 1300 and stored in the computer memory 1120 with the respective location data 1124a.

At the step 506, the processor 1110 accesses the event data 1122 and the perception data 1124 and determines correlations between the event data 1122 and the perception data 1124 at both the location level and a multi-location level. In other words, the processor 1110 may determine what effect the various event data 1122 (and combinations of the event data 1122) has on patient satisfaction at both the location level and a multi-location level. As an example, the processor 1110 could potentially determine that for patients with a certain medical condition, awards received by the facilities and advertising expenditures have a great effect on patient satisfaction. And for patients with other certain medical conditions, activations of nurse call lights may have an enhanced relationship to patient satisfaction. Or that satisfaction of patients within a facility (or at the multi-location level) is closely tied to staffing levels and certain demographics. Conversely, the processor 1110 could determine that satisfaction of patients within a facility (or at the multi-location level) is only very loosely (or even apparently unrelated) to certain staffing levels, amenities, or demographics. These are of course only examples.

At the step 508, the processor 1110 determines proposals 1127 at both the location level and the multi-location level to improve patient satisfaction based on the correlations determined at step 506. So, for example, the processor 1110 may determine that staffing levels and advertising should be increased (either inside a facility or across multiple facilities), patients in certain demographics (e.g., the elderly) should be given additional attention (either inside a facility or across multiple facilities), that certain amenities should be reduced (either inside a facility or across multiple facilities), and that a thermostat should be serviced in a certain patient room. If the pricing/cost module is used, the estimated cost of taking these actions may be determined and considered in foil ling the proposals 1127.

At the step 510, the processor 1110 actuates the at least one output device 1400 to convey the proposal(s) 1127 to a user.

At the step 512, the processor 1110 may receive user input containing various proposed event data (e.g., increasing staffing levels, increasing amenities, decreasing advertising) from at least one of the input devices 1500 and stores the proposed event data in the computer memory 1120. Then at step 514, the processor 1110 estimates patient satisfaction based on the proposed event data and the at least one correlation from step 506. The processor 1110 then actuates the at least one output device 1400 at step 516, conveying the estimated patient satisfaction to the user and allowing the user to see the likely outcomes in patient satisfaction if various actions (represented by the proposed event data) are taken. The hospital system may then choose to enact policies in line with the proposals 1127 or the proposed event data.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention. It will be understood that certain features and subcombinations are of utility and may be employed without reference to other features and subcombinations and are contemplated within the scope of the claims. Various steps in described methods may be undertaken simultaneously or in other orders than specifically provided. While various software have been described as enabling specific functions, those skilled in the art will appreciate that files and software may be commingled or further segregated, and that specific file or software labels are used for convenience.

We claim:

1. A system for evaluating a patient's perception of care provided at a healthcare facility, the system comprising:
   at least one care event device that generates quantitative care event data regarding the patient's care at the healthcare facility,
   wherein said at least one care event device includes each of the following:
      a nurse call system, whereby the patient activates the nurse call system to request care from a caregiver, and wherein the care event data generated by the nurse call system includes information indicative of the patient activating the nurse call system,
      a real-time locating system for locating the caregiver and the patient within the healthcare facility, wherein the care event data generated by the real-time locating system includes information indicative of a location of the caregiver and the patient within the healthcare facility, and
      an interactive patient bed, wherein the care event data generated by the interactive patient bed includes information indicative of the patient exiting the bed and a status of the bed; and
   a patient perception input interface, whereby the patient is presented with one or more questions related to the patient's care provided by the healthcare facility or the caregiver and further whereby the patient provides responses to said one or more questions,
   wherein said responses provide qualitative patient perception data representing the patient's perception of the care provided at the healthcare facility,
   wherein the system is programmed to:
      access the quantitative care event data and the qualitative patient perception data;
      present, on an electronic display, a visual association of at least a portion of the quantitative care event data with at least a portion of the qualitative patient perception data;
      perform a correlation analysis that compares the qualitative patient perception data against the quantitative care event data;
      in response to said correlation analysis, identify at least one correlation between said quantitative care event data and said qualitative patient perception data, and based on said identified correlation, determine the patient's perception of care provided by the healthcare facility.

2. The system of claim 1,
   wherein the identified at least one correlation determines an affect of the quantitative care event data on the patient's perception of care provided by the healthcare facility; and
   wherein the system is programmed to, in response to identifying said at least one correlation, determine at least one proposal based on said correlation to improve patient satisfaction.

3. The system of claim 2, wherein the system is programmed to estimate a patient satisfaction of the patient's care at the healthcare facility in view of the at least one proposal.

4. The system of claim 3, wherein said determining at least one proposal is based, at least in part, on a cost estimate for an action associated with the proposal.

5. The system of claim 1, wherein the system is programmed to receive information indicative of a unique patient identifier associated with the patient.

6. The system of claim 1, wherein the system is programmed to present, on an electronic display, a visual association of the information indicative of the location of the patient within the healthcare facility with at least one of (i) the quantitative care event data regarding the patient's care at the healthcare facility, or (ii) the qualitative patient perception data representing the patient's perception of the care provided at the healthcare facility,
   wherein the presenting on the electronic display the visual association is performed in generally real time as said location of the patient and said at least one of the quantitative data is generated by the care event device or the qualitative data is input to the patient input interface.

7. The system of claim 1, wherein the patient perception input interface is associated with either of the patient or the caregiver.

8. The system of claim 7, wherein said one or more questions related to the patient's care and presented to the patient via the patient input interface request patient perception data related to at least one of the following: the patient's perception of an attentiveness of the caregiver, the patient's perception of a responsiveness of the caregiver, the patient's perception of pain management, the patient's perception of a comfort of the healthcare facility, the patient's perception of amenities of the healthcare facility, and the patient's perception of a prestige of the facility.

9. A method of collecting disparate types of patient data and using said collected patient data to evaluate a patient's perception of care provided at a healthcare facility, the method comprising the steps of:
   collecting quantitative care event data regarding the patient's care at the healthcare facility, wherein the quantitative care event data is generated by at least one care event device, and wherein said at least one care event device is at least one of the following:
      a nurse call system, whereby the patient activates the nurse call system to request care from a caregiver,
      a real-time locating system that locates the caregiver and the patient within the healthcare facility, and
      an interactive patient bed, wherein the care event data generated by the interactive patient bed includes information indicative of the patient exiting the bed and a status of the bed;
   collecting qualitative patient perception data from the patient,
   wherein said step of collecting patient perception data includes presenting, to the patient, one or more questions related to the patient's care provided by the healthcare facility or a caregiver;
   performing a correlation analysis that compares said quantitative care event data against said qualitative patient perception data;

in response to said correlation analysis, identifying at least one correlation between said quantitative care event data and said qualitative patient perception data; and based on said identified correlation, determining the patient's perception of care provided by the healthcare facility.

10. The method of claim 9, wherein the at least one care event device is the nurse call system, and the collected care event data generated by the nurse call system includes information indicative of the patient activating the nurse call system.

11. The method of claim 9, wherein the at least one care event device is the real-time locating system, and the collected care event data generated by the real-time locating system includes information indicative of a location of the caregiver and the patient within the healthcare facility.

12. The method of claim 11, further including the step of providing an electronic display that presents a visual association of the information indicative of the location of the patient within the healthcare facility with at least one of (i) the quantitative care event data regarding the patient's care at the healthcare facility, or (ii) the qualitative patient perception data representing the patient's perception of the care provided at the healthcare facility.

13. The method of claim 12, wherein the visual association presented on the electronic display is indicative of a generally real time relationship of the location of the patient within the healthcare facility to said at least one of the quantitative care event data or the qualitative patient perception data.

14. The method of claim 9, further including the step of providing an electronic display on which is presented a visual association of at least a portion of the quantitative care event data with at least a portion of the qualitative patient perception data.

15. The method of claim 9, wherein the identified at least one correlation provides information on how the collected quantitative care event data affects the patient's perception of care provided by the healthcare facility.

16. The method of claim 15, further including the step of determining at least one proposal, based on said correlation, to improve patient satisfaction.

17. The method of claim 16, further including the step of estimating a patient satisfaction of the patient's care at the healthcare facility in view of the at least one proposal.

18. The method of claim 16, wherein said determining at least one proposal is based, at least in part, on a cost estimate for an action associated with the proposal.

19. The method of claim 9, wherein said one or more questions related to the patient's care request patient perception data related to at least one of the following: the patient's perception of an attentiveness of the caregiver, the patient's perception of a responsiveness of the caregiver, the patient's perception of pain management, the patient's perception of a comfort of the healthcare facility, the patient's perception of amenities of the healthcare facility, and the patient's perception of a prestige of the facility.

* * * * *